(12) United States Patent
Sprachman et al.

(10) Patent No.: US 10,975,407 B2
(45) Date of Patent: Apr. 13, 2021

(54) COMPOSITION FOR USE IN MOLECULAR CHAIN SYNTHESIS

(71) Applicant: The Charles Stark Draper Laboratory, Inc., Cambridge, MA (US)

(72) Inventors: Melissa M. Sprachman, Cambridge, MA (US); Andrew P. Magyar, Acton, MA (US); Kettner John Frederick Griswold, Jr., Brookline, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 54 days.

(21) Appl. No.: 16/311,477

(22) PCT Filed: May 22, 2017

(86) PCT No.: PCT/US2017/033772
§ 371 (c)(1),
(2) Date: Dec. 19, 2018

(87) PCT Pub. No.: WO2017/222711
PCT Pub. Date: Dec. 28, 2017

(65) Prior Publication Data
US 2019/0323049 A1    Oct. 24, 2019

Related U.S. Application Data

(60) Provisional application No. 62/353,318, filed on Jun. 22, 2016, provisional application No. 62/398,049, filed on Sep. 22, 2016.

(51) Int. Cl.
| C07H 21/02 | (2006.01) |
| C07H 21/04 | (2006.01) |
| C12P 19/34 | (2006.01) |
| C12P 21/00 | (2006.01) |

(52) U.S. Cl.
CPC ............... *C12P 19/34* (2013.01); *C12P 21/00* (2013.01)

(58) Field of Classification Search
None
See application file for complete search history.

(56) References Cited

U.S. PATENT DOCUMENTS

| 8,808,989 B1 | 8/2014 | Efcavitch et al. |
| 2016/0046973 A1 | 2/2016 | Efcavitch et al. |

FOREIGN PATENT DOCUMENTS

| WO | WO2000053805 | 9/2000 |
| WO | WO2006013110 | 2/2006 |
| WO | WO2008042067 | 4/2008 |
| WO | WO2008112980 | 9/2008 |
| WO | WO2010025310 | 3/2010 |
| WO | WO2013131888 | 9/2013 |

OTHER PUBLICATIONS

Singh et al. C. R. Chimie (2005), vol. 8, pp. 789-796 .*
International Preliminary Report on Patentability, dated Jan. 3, 2019, from International Application No. PCT/US2017/033770, filed on May 22, 2017. 9 pages.
International Preliminary Report on Patentability, dated Jan. 3, 2019, from International Application No. PCT/US2017/033772, filed on May 22, 2017. 8 pages.
Anonymous, "Pacific Biosciences Develops Transformative DNA Sequencing Technology," Pacific Biosciences Technology Backgrounder, Nov. 24, 2008.
Chow, B.Y. et al., "Photoelectrochemical synthesis of DNA microarrays," PNAS 106(36):15219-15224, Sep. 8, 2009.
Dodge, A. et al., "A Microfluidic Platform Using Molecular Beacon-Based Temperature Calibration for Thermal Deybridization of Surface-Bound DNA," Anal. Chem. 76(6):1778-1787, Mar. 15, 2004.
Huang, Y. et al., "Solvent resistant microfluidic DNA synthesizer," The Royal Society of Chemistry, 7:24-26, Nov. 30, 2006.
International Search Report and the Written Opinion of the International Searching Authority, dated Jul. 19, 2017, from International Application No. PCT/US2017/033772, filed on May 22, 2017. 10 pages.
International Search Report and the Written Opinion of the International Searching Authority, dated Aug. 25, 2017, from International Application No. PCT/US2017/033770, filed on May 22, 2017. 10 pages.
Lee, C.-C. et al., "A microfluidic oligonucleotide synthesizer," Nucleic Acids Research, 38(8):2514-2521, Feb. 21, 2010.
Solgaard, O. et al., "Optical MEMS: From Micromirrors to Complex Systems," Journal of Microelectromechanical Systems, 23(3):517-538, Jun. 1, 2014.

\* cited by examiner

*Primary Examiner* — Patrick T Lewis
(74) *Attorney, Agent, or Firm* — Houstonhogle LLP (57) ABSTRACT

A composition for use in extending a molecular chain includes a carrier group and a payload group. The carrier group comprising a signaling group and a blocking group. A first bond bonds the payload group to the carrier group and a second bond bonds the signaling group to the blocking group. The first and second bonds are selectively cleavable such that the first bond is cleavable without cleaving the second bond. The payload group is to be attached to the molecular chain, while the blocking group is to block further attachments to the molecular chain once the payload group has been attached. The signaling group comprises a photon emitter that emits a signature photon in response to interrogation by an interrogatory photon. The carrier group transitions from a loaded state to an empty state upon cleavage of the first covalent bond.

17 Claims, 7 Drawing Sheets

COMPOSITION FOR USE IN MOLECULAR CHAIN SYNTHESIS

RELATED APPLICATIONS

This application is a § 371 National Phase Application of International Application No. PCT/US2017/033772, filed on May 22, 2017, now International Publication No. WO 2017/222711 A1, published on Dec. 28, 2017, which International Application claims the benefit under 35 USC 119(e) of U.S. Provisional Application Nos. 62/353,318, filed Jun. 22, 2016, and 62/398,049, filed on Sep. 22, 2016. All of the above-mentioned applications are incorporated herein by reference in their entirety.

FIELD OF INVENTION

The invention relates to synthesis of molecular chains, and in particular to single-stranded DNA.

BACKGROUND

It is known in the art to take a strand of DNA and identify the sequence of base pairs. This process, known as "sequencing," has been helpful in promoting the understanding of genetics.

It is desirable to not only know what base pairs are in naturally-occurring DNA but to be able to synthesize new strands of DNA with one's own choices for base pairs. The ability to do so could give rise to many commercial and medical applications.

Known methods of attaching nucleotides include standard phosphoramidite solid phase synthesis. An alternative method involves the use of printed DNA microarrays in connection with enabling chip-based chemical DNA synthesis with error correction. Both of these methods rely on phosphoramidite chemistry.

SUMMARY

In one aspect, the invention features a composition of matter for use in extending a molecular chain. Such a composition includes a payload group to be attached to the molecular chain and a carrier group that brings the payload group to the molecular chain. A signaling group and a blocking group together form this carrier group. A first bond bonds the payload group to the carrier group, and a second bond bonds the signaling group and the blocking group to each other. These bonds are selectively cleavable such, without cleaving the second bond, it is possible to transition the carrier group from a loaded state to an empty state by cleaving only the first bond. The blocking group blocks further attachments to the molecular chain once the payload group has been attached to the molecular chain. The signaling group includes a photon emitter that emits a signature photon in response to interrogation by an interrogatory photon.

Among these are compositions in which the carrier group transitions to the empty state via electrochemical cleavage of the first covalent bond, those in which it does so as a result of a change in oxidation state of the carrier group, and those in which it does so as a result of acceptance of an electron either by the carrier group or by the blocking group. In some of these embodiments, the composition includes a reducing agent for supplying an electron, or a shuttle molecule for ferrying an electron from an electron source to the carrier group.

Also among the embodiments of the composition are those in which the signaling group includes a fluorophore, and those in which the signaling group includes a radiating group that is configured to emit a signature photon in the visible light range in response to an interrogatory photon.

Other embodiments of the composition are those in which the payload group includes a nucleotide, in which case the molecular chain is a single-strand of DNA, and those in which the payload group includes an amino acid, in which case the molecular chain is a protein or peptide.

The method is applicable to the assembly of many kinds of molecular chain. For example, in some practices, the molecular chain is a single-strand of DNA, in which case the payload is a nucleotide. However, it is also possible to assemble a protein in this manner, in which case the payload would be an amino acid. More generally, the method is applicable to the assembly of any polymer in which the monomers are to be attached in a particular sequence. In such a case, each payload is a monomer.

These and other features of the invention will be apparent from the following detailed description and the accompanying figures, in which:

DETAILED DESCRIPTION

The apparatus and methods described herein are configured to build a chain of nucleotides one step at a time in a way that includes confirming, at each step, that the desired nucleotide has indeed been added to the chain. The procedure is carried out through microfluidically controlled introduction of the nucleotide and a suitable enzyme, such as Terminal deoxynucleotidyl transferase (TdT), for attaching the nucleotide to the growing chain.

Figure 1:
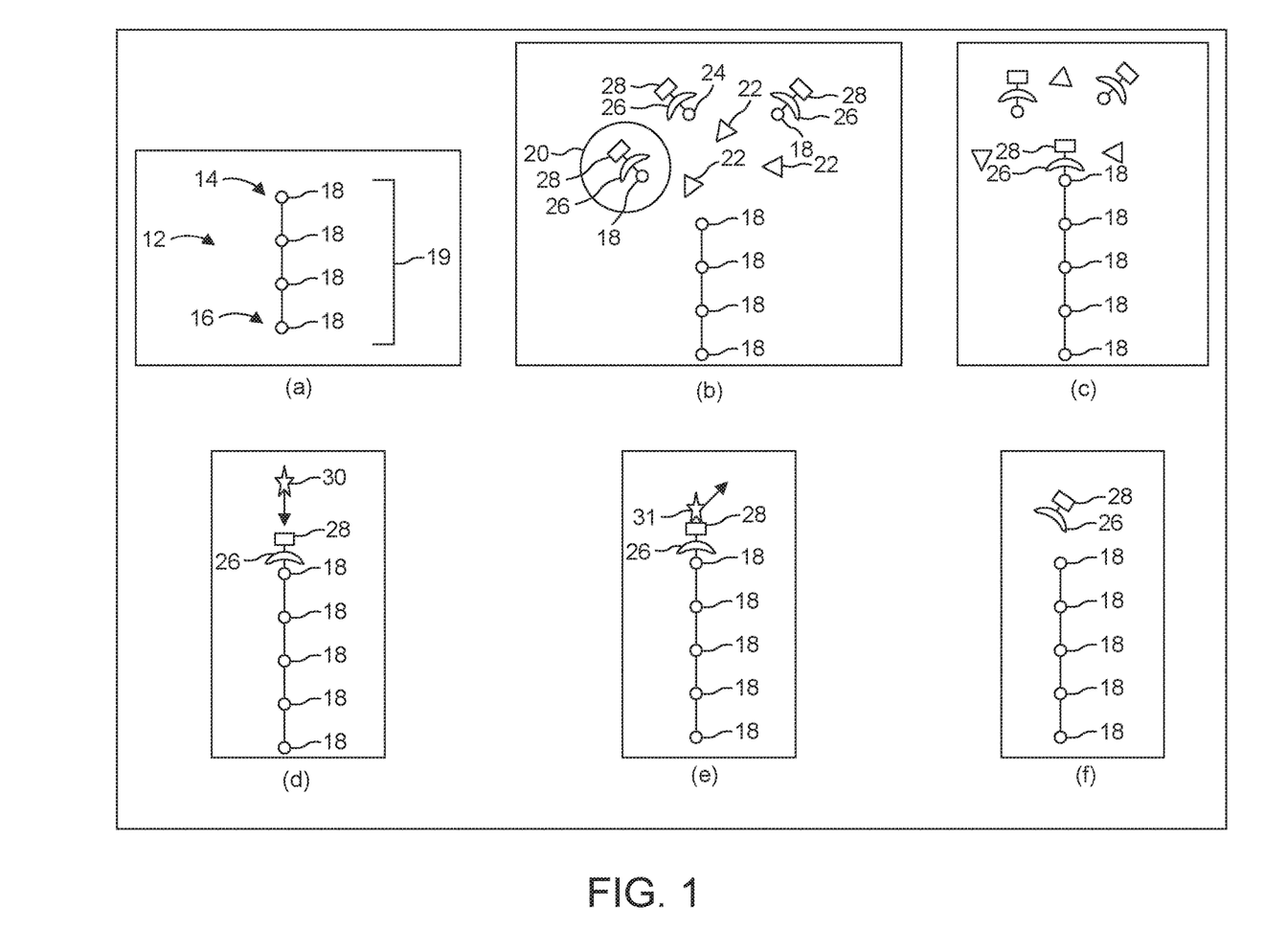
FIG. 1 shows snapshots of certain events that occur during attachment of a monomer to an oligomer strand.

FIG. 1 shows steps to be carried out add a single nucleotide 18 to the chain 12. The steps shown in FIG. 1 are thus repeated for each nucleotide 18 to be added.

In step(a), FIG. 1 shows a DNA strand 12 having a first end 14 and a second end 16, one of which is tethered to a surface. Between the first and second ends 14, 16 is a growing sequence 19 of nucleotides 18.

The process of synthesizing the DNA strand 12 involves repeatedly attaching additional nucleotides 18 to the first end 14 until one has attained a nucleotide sequence 19 having a desired arrangement. In a typical embodiment, the first end 14 corresponds to the 3' end, in which case the second end 16 corresponds to the 5' end. However, in other embodiments, the first end 14 corresponds to the 5' end, in which case the second end 16 corresponds to the 3' end.

A typical nucleotide sequence 19 may have thousands of nucleotides 18. Since the synthesis procedure involves adding one nucleotide 18 at a time, it is important to be able to add nucleotides 18 quickly. The functionality of a DNA strand 12 depends a great deal on the absence of any errors in the nucleotide sequence 19. Even a small error is enough to impair, if not destroy, a DNA molecule's functionality. Thus, a practical synthesizer must be both fast, reliable, and able to fix errors as they occur.

The procedure for attaching a particular nucleotide 18 to the first end 14 includes exposing the first end 14 to a solution that contains many molecules of a loaded carrier 20 and many molecules of an enzyme 22, as shown in step (b). A suitable enzyme 22 is a naturally-occurring enzyme, such as TdT, or a modified version of such an enzyme.

Each carrier 20 includes a blocking group 26 appended to a signaling group 28. In the embodiment described herein, the signaling group 28 carries one fluorophore. The carrier 20 exists in two states: a loaded state, and an empty state. In the loaded state, the carrier 20 covalently bonds to its payload. In the empty state, the carrier 20 is no longer bonded to its payload, and can therefore accept a new payload. In the illustrated embodiment, the payload is any one of the naturally occurring nucleotides 18.

To transition from the loaded state to an empty state, the carrier 20 undergoes a cleaving of a covalent bond between itself and its payload. This covalent bond is configured such that the cleavage mechanism will cleave this bond while leaving other bonds undisturbed. The cleaving can be carried out in a variety of ways. For example, it is possible to illuminate the carrier 20 with photons of appropriate energy, thus promoting optical cleavage. Additionally, it is possible to chemically cleave this bond.

A suitable cleaving method is an electrochemical one as described in connection with FIGS. 2 and 3. In the case of such electrochemical cleavage, the covalent bond is configured to cleave while leaving other bonds undisturbed by having the reduction potential required to cleave this covalent bond be lower than that required to cleave the bond between the blocking group 26 and the signaling group 28. This ensures that the cleavage mechanism will detach only the payload while leaving the signaling group 28 and the blocking group 26 still attached to each other.

The carrier 20 can carry any of the naturally occurring nucleotides 18. Thus, in order to attach, for example, guanine to the growing DNA strand 12, one would flood the environment with many loaded carriers 20 that are carrying guanine. Then, to attach, for example, cytosine on top of the guanine on the DNA strand 12, one would rinse away any loaded carriers 20 carrying guanine, and then flood the environment with a whole new set of loaded carriers 20, this time carrying cytosine instead. This permits the serial attachment of different kinds of nucleotide 18 to the growing DNA strand 12.

Attachment to the DNA strand 12 does not happen instantly. Thus, the next step is to wait for a pre-determined attachment interval. This interval is long enough so that it is very likely that one of the enzymes 22 and one of the loaded carriers 20 will encounter each other at the first end 14 of the growing DNA strand 12. When this happens, the enzyme 22 causes the loaded carrier 20 to attach to the first end 14, as shown in step (c).

As noted above, the loaded carrier 20 comes with a blocking group 26. It is at this point that the blocking group 26 comes into play. Once one loaded carrier 20 has been attached to the DNA strand 12, its associated blocking group 26 prevents any further loaded carriers 20 from attaching themselves.

After having waited for the full attachment interval, there is still a possibility that nothing was able to attach to the first end 14. It is therefore important to confirm that the loaded carrier 20 did in fact attach to the first end 14.

As noted above, the carrier 20 also contains a signaling group 28. It is at this point that the signaling group 28 becomes necessary.

The signaling group's fluorophore emits a signature photon 31 in response to illumination by an interrogatory photon 30. The process of illuminating the fluorophore with an interrogatory photon 30 will be referred to herein as "interrogation." The resulting emission of a signature photon 31 is a "response."

Each carrier 20 in solution has its own signaling group 28 with its own fluorophore. To avoid detection of spurious signature photons 31, these should all be rinsed away before interrogation. If attachment was successful, there will be one signaling group 28 remaining, namely the one belonging to the signaling group 28 of whichever carrier 20 ultimately attached to the DNA strand 12, bringing the newly-added nucleotide 18 with it.

An interrogation takes place, as shown in step (d), after the flushing step. This involves illuminating the DNA strand 12 with interrogatory photons 30 to excite an electron in the fluorophore to a higher energy level, and then attempting to detect the signature photon 31 emitted as this electron decays to its ground state, as shown in step (e). Since only one signature photon 31 can be emitted, collection efficiency is quite important. Even with high collection efficiency, it is often necessary to repeatedly interrogate.

If, after repeated interrogation, no signature photon 31 is detected, one can infer that nothing was able to attach to the first end 14. Therefore, another attempt must be made to attach the carrier 20.

On the other hand, if a signature photon 31 is detected, one can infer that the carrier 20 is now attached to the first end 14 of the DNA strand 12. At this point, both the signaling group 28 and the blocking group 26 have done their job. These must then be removed for three reasons. First, their presence in the finished product may interfere with its function. Second, if the blocking group 26 remains, no further attachments can occur. And third, if the signaling group 28 remains, its fluorophore may emit signature photons 31 during subsequent interrogation phases. This will cause confusion since a detector would have no way of knowing where a photon was coming from.

The next step is therefore to detach the carrier 20, as shown in step (f). This is best carried out electrochemically as described below. The reduction potential of the bond between the signaling group 28 and the blocking group 26 differs from that of the bond between the carrier 20 and its payload, the nucleotide 18. This ensures that the signaling group 28 and the blocking group 26 will be removed together as a unit. Removing the carrier 20 thus results in only the nucleotide 18 remaining at the first end 14 of the DNA strand 12.

However, other embodiments contemplate detaching the carrier 20 in other ways. For example, it is possible to use a purely chemical or purely optical mechanism for detaching the carrier 20.

After this electrochemical detaching step, it is useful to confirm that the signaling group 28 and the blocking group 26 have in fact been removed. The same interrogation procedure described above in connection with step (d) can then be carried out. If the signaling group 28 is no longer attached, there will be no response. Hence, one can infer, from the absence of any response, that the strand 12 is now ready for the next desired nucleotide 18. On the other hand, if a signature photon 31 is detected, one simply repeats the electrochemical detaching step. As described below, the signaling group 28 is appended covalently to blocking group 26. Therefore, if the signaling group 28 is not present, one can reasonably infer that the blocking group 26 is also no longer present.

A suitable mechanism to load an empty carrier 20 with a nucleotide 18 is to covalently link the nucleotide's 3' hydroxyl group to a fluorophore-substituted benzoquinone via a cleavable functional group. One example of such a cleavable functional group is a quinone oxime ether. Another is an ester that is designed to undergo spontaneous lactonization/cleavage upon quinone reduction.

To unload the carrier 20, one can unblock the 3' hydroxyl group through electrochemical reduction. Such electrochemical reduction can be carried out by providing a source and sink for electrons to be used in the electrochemical reaction. One way to provide a source and sink for electrons is to provide electrodes in contact with a suitable medium. In some cases, it may be useful to provide an electron transport shuttle molecule to transfer electrons between the electrodes and the reaction site. An alternative is to provide a reducing molecule in the solution. With the 3' hydroxyl group having been unblocked, it becomes possible to rinse away the fluorophore-containing product that results from reduction, examples of which include an aminophenol or a chroman-2-one.

A cleavable group can be made in any of a variety of ways. One example, shown in FIG. 2, features a complex in which the cleavable group is a quinone oxime ether and in which the nucleotide has an aminooxy substitution at the 3' position. In the particular embodiment shown, the carrier 20 is made by introducing benzoquinone that has been modified to include a linker 24 appended to a fluorophore 28. A suitable linker 24 is one made of repeating methylene or ethylene glycol units and terminated with a functional group that can be easily modified to contain a fluorophore. One of many examples of such a functional group is a primary amine, which can be made to react with a N-hydroxysuccinimidyl ester-modified fluorophore. This is followed by forming a benzoquinone oxime ether. Such an ether can be formed by condensing the benzonquinone with the aminooxy group.

When the time comes to unblock the DNA strand 12, for example during step (f) of FIG. 1, one cleaves the bond between the nitrogen and the oxygen. This, in turn, releases the fluorophore-substituted aminophenol, which can then just be rinsed from the system. In some embodiments, the actual cleaving of the bond between the nitrogen and the oxygen is carried out by exposure to a potential difference for a suitable period in a buffered solution. In some examples, this is carried out by exposure to a potential difference of 100 mV for 60 seconds in a slightly alkaline phosphate buffered solution, i.e. one that is maintained at pH 7.4. However, it is also possible to carry out this cleavage in other ways. One way is to include a suitable reducing agent in solution.

Figure 3:
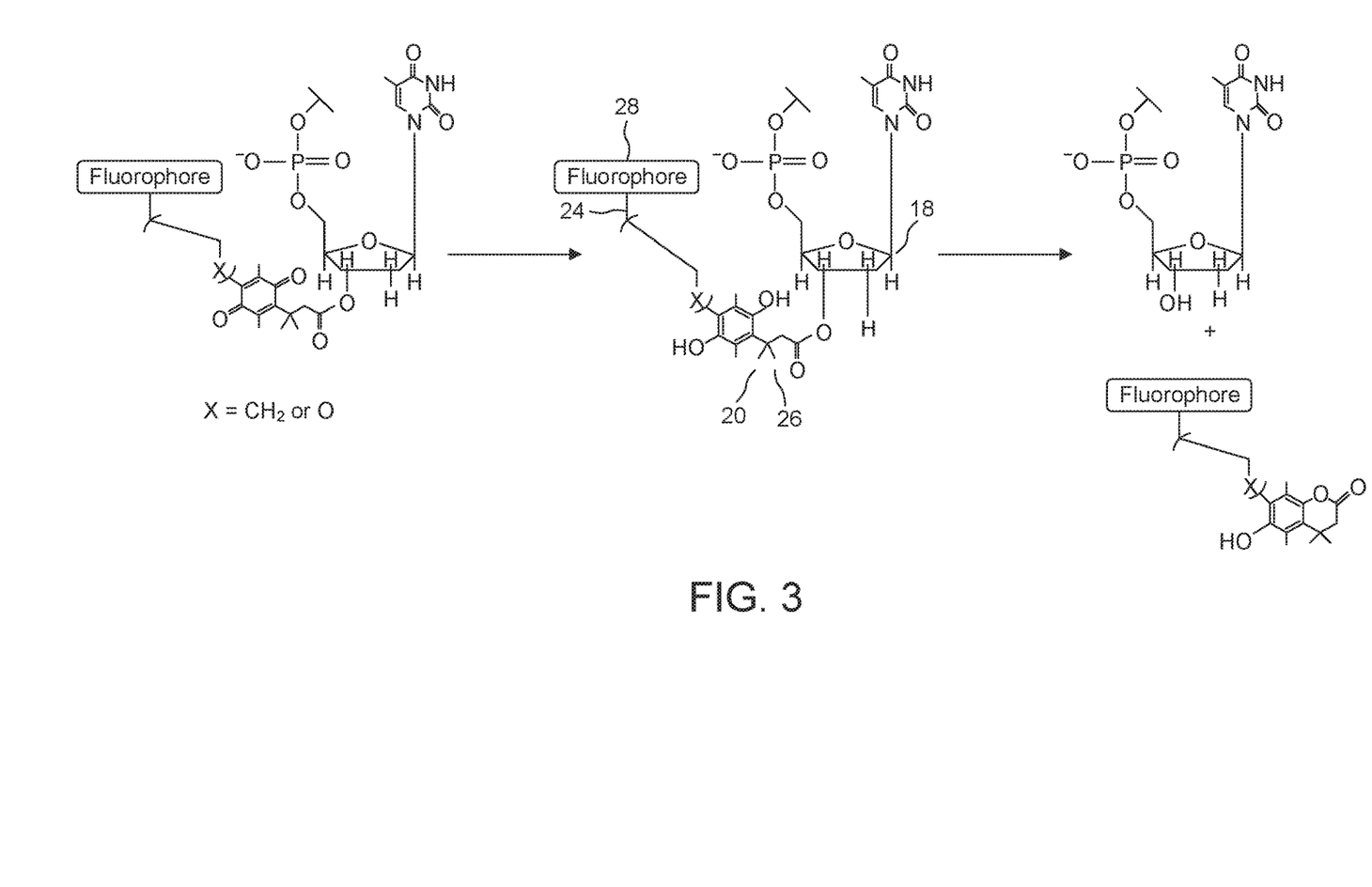

Another one of the many embodiments can be seen in FIG. 3. This particular embodiment features a complex in which the cleavable group is designed to undergo spontaneous lactonization upon quinone reduction.

This embodiment involves bonding the nucleotide's 3' hydroxyl group with a quinone. The quinone has been modified to have a functional group that has been selected to encourage 6-membered ring formation upon reduction. This functional group is a 3-(2,5-dimethyl-3,6-dioxocyclohexa-1,4-dien-1-yl)-3-methylbutanoic ester. The quinone has also been further modified to have a linker 24 that is appended to a fluorophore 28, similar to that shown in FIG. 2. Electrochemical reduction, as described in connection with FIG. 2, involve acceptance of an electron by a chemical species. This electron is provided by some electron source, such as an electrode or a reducing agent in solution. In the particular embodiment described herein, the electron reduces benzoquinone. This results in formation of hydroquinone. Once formed, the hydroquinone spontaneously lactonizes to form a chroman-2-one. As it does so, it reveals the free 3' hydroxyl group of the nucleotide 18.

Figure 4:
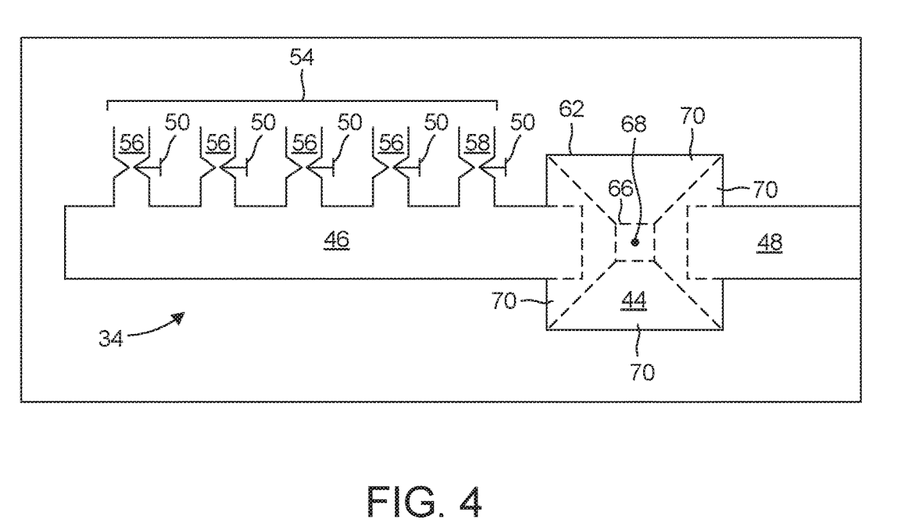
FIGS. 4 and 5 show top and side views of a synthesizer for carrying out the procedure shown in FIG. 1.

Referring to FIG. 4, a suitable synthesizer 32 for implementing the procedure described in connection with FIG. 1 features a microfluidic system 34, an excitation system 36, and a detection system 38. A processor 40 connected to each of these systems 34, 36, 38 controls operation of the synthesizer 32.

The microfluidic system 34 is etched from a substrate 42, such as a silicon substrate. This is advantageous because such a substrate 42 is rigid and able to sustain high pressures. The use of high-pressure permits higher velocity liquid flow and hence greater throughput. This greater throughput will permit assembly of a DNA strand 12 at the rate of on the order of $10^4$ nucleotides per day, or approximately one nucleotide attachment every ten seconds. The absence of any significant porosity of such a substrate 42 is likely to suppress absorption or trapping of the various substances that are used during the procedure, such as a nucleotide 18. In addition, the naturally occurring crystalline planes permit fabrication of nearly perfect optical surfaces, thereby promoting greater collection efficiency.

Etching can be carried out using a dry etching technique, for example by exposing the substrate to reactive ions. However, it is difficult to make a sloping sidewall and smooth surfaces using this method.

Another etching method is a wet etch in which the etching rate is different along different directions of the crystal. Such anisotropic etching can be carried out using a solution of potassium hydroxide. In this type of etching, the 111 facet is the slowest to etch. For silicon, this results in sidewalls 70 at a 54.7-degree angle.

Another etching method substitutes tetramethylammonium hydroxide for potassium hydroxide, particularly with an agent for reducing surface tension. This permits better control over the device geometry, and in particular, the ability to expose crystalline surfaces, such as the surface associated with the crystal's 110 plane. Crystalline surfaces are particularly advantageous for collection of photons because they form nearly perfect optical surfaces.

The microfluidic system 34 includes a synthesizing chamber 44 in which the attachment of additional nucleotides 20 to the first end 14 takes place. A first channel 46 brings incoming media to the synthesizing chamber 44 and a second channel 48 takes outgoing media from the synthesizing chamber for disposal or recycling.

The first channel 46 connects the synthesizing chamber 44 to a plurality of media sources 54. These include plural loaded-carrier sources 56, each of which supplies a carrier 20 loaded with a corresponding one of a plurality of naturally-occurring nucleotides 18. Also included is a flushing-medium source 58 that connects to a source of flushing medium, as well as an engineered-enzyme source 59. Each media source 54 has a corresponding valve 50 for selectively connecting that source 54 to the first channel 46.

The excitation system 36 includes a light source 60 disposed to be in optical communication with the signaling group 28. During fluorophore interrogation, the processor 40 causes the light source 60 to provide a pulse of light in an effort to excite the fluorophore within the signaling group 28. Once the excitation pulse is complete, the detection system 38 takes over and waits for the fluorophore to respond with its signature photon 31.

Figure 5:
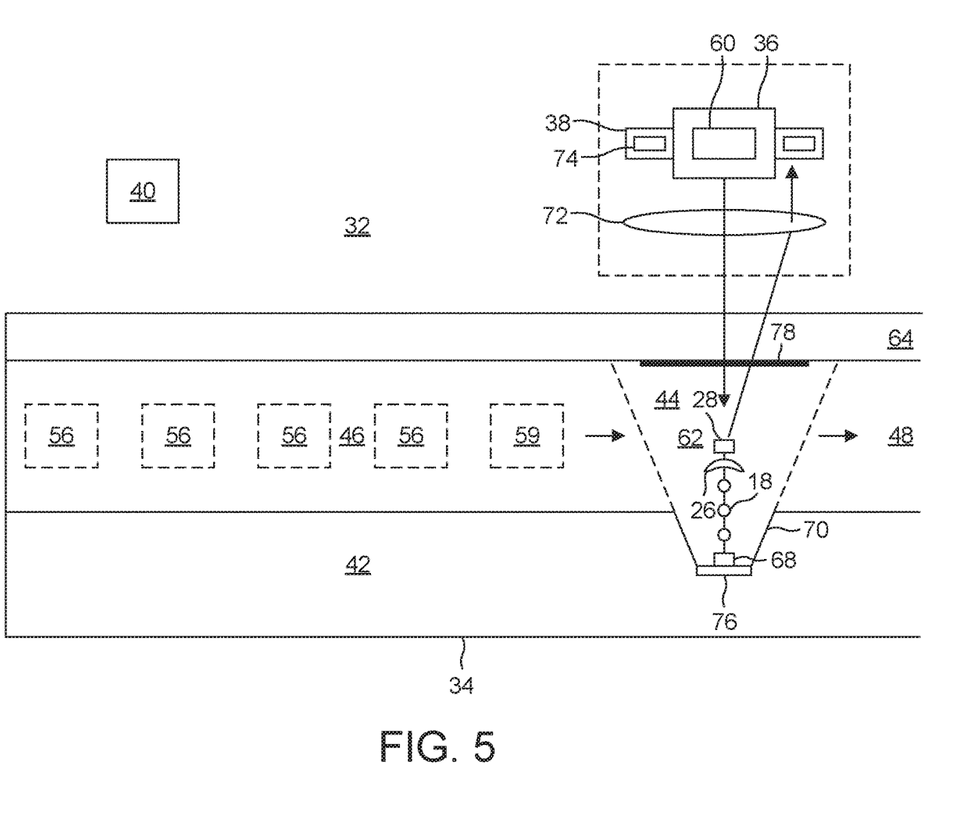

In the first embodiment, the synthesizing chamber 44 takes the form of a well 62 with a glass cover 64. The well 62 has a floor 66 having a functionalized spot 68 to which the second end 16 of the DNA strand 12 attaches. A suitable procedure for forming the functionalized spot 68 is to use an electron beam or an ion beam to place nanopatterned carbon dots on the floor 66 and to then carry out amine functionalization of the carbon dots by exposing them to an ionized ammonia gas.

Since the second end 16 is tethered to the functionalized spot 68, and since nucleotides 18 are being added to the first end 14, it follows that the position from which the signature photon 31 begins its journey to the detector 74 changes with every nucleotide 18 added. This means that the detection system 38 must be able to efficiently detect single photons from a volume that is large enough to fit the entire DNA strand 12 being built. This volume would be on the order of a cubic micrometer.

To promote collection efficiency, the functionalized spot 68 should be centered within the well 62. However, if the well 62 is sufficiently deep, loss of collection efficiency is relatively minor. For example, in the case of a 20 micrometer deep well 62 that is 5 microns wide at its floor 66, placing the functionalized spot 68 at the edge of the well's floor reduced collection efficiency from 98% to 95%.

The distance between the glass cover 64 and the floor 66 is sufficient to avoid effects of surface flow. Although it is possible for the well 62 to be deeper than necessary, there is no particular advantage to such additional depth. A suitable depth for a well that is less than 5 micrometers wide is 10 micrometers for a collection optic having a numerical aperture of at least 0.9 and a device with 54.7 degree sidewalls. A suitable lineal dimension for the well 62 at the plane at which it meets the glass cover 64 is about 50 micrometers.

Although the sidewalls 70 only approximate a paraboloid, they are nevertheless sloped sufficiently to function in a manner similar to a paraboloid. As a result, light emitted by the fluorophore 28 tends to be reflected towards a microscope lens 72 disposed above the glass cover 64. The microscope lens 72 then relays the light to a detector 74. This propensity to guide emitted light towards the detector 74 results in a highly efficient detection system 38.

The detector 74 is one that is optimized for detecting a single photon. A suitable detector 74 is one based on an avalanche photodiode. In the illustrated embodiment, the microscope lens 72 directs the received signature photon 31 to the detector 74. However, in other embodiments, a fiber probe delivers the signature photon 31 to the detector 74. And in still other embodiments, an active area of a single-photon detector 74 that has been placed immediately above the well receives the signature photon 31.

The synthesizer 32 also includes a mechanism for creating an electrical potential across the well 62. This is useful for cleaving the blocking group 26 off the strand 12 after having confirmed attachment of the carrier 20. In one embodiment, a first electrode 76 at the floor 66 and a second electrode 76 at the glass cover 64 provide a source and sink of electrons for electrochemical cleaving. A suitable first electrode 76 is an aluminum ground plane. Because of its location on the glass cover 64, the second electrode 78 is transparent. A suitable transparent second electrode 78 is one made of indium tin oxide. The electrodes are maintained at an applied voltage is sufficient to ensure an abundant supply of electrons to be used in the electrochemical cleavage discussed in connection with FIGS. 2 and 3. This voltage is applied during step (f) in FIG. 1, which comes prior to the introduction of the next nucleotide 20 that is to be attached. It is removed when no electrochemical cleavage is desired. This would correspond to steps (a)-(e) in FIG. 1.

Figure 6:
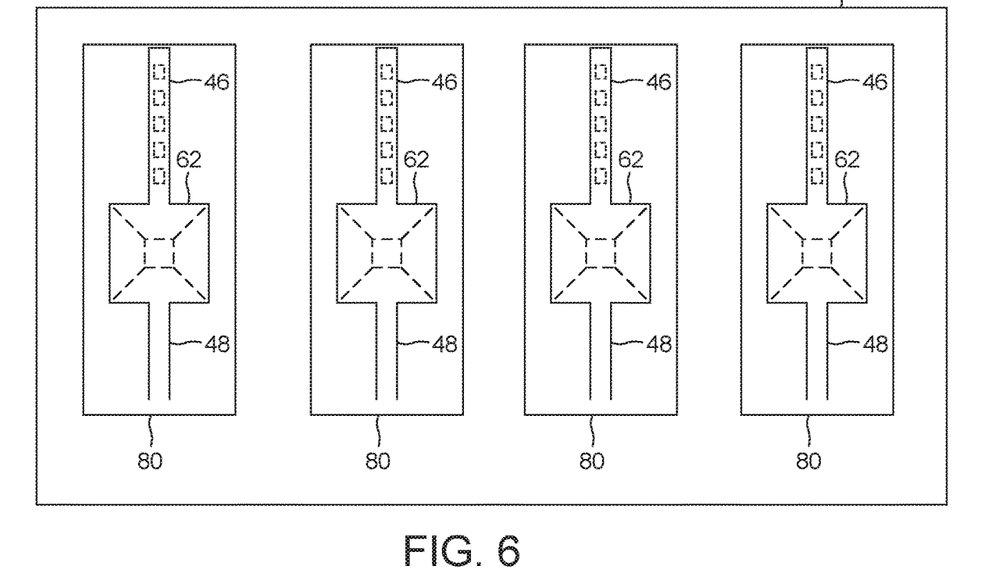
FIG. 6 shows an embodiment having multiple instances of synthesizing chambers for use in mass production.

The channels 46, 48, the well 62, and the associated valves 50 define one manufacturing unit 80. This manufacturing unit 80 is modular and can be repeated multiple times on the same substrate, as shown in FIG. 6. This permits mass-production of DNA strands. In some embodiments, the valves 50 associated with each manufacturing unit 80 are independently controlled. This means that, in an array of manufacturing units 80 shown in FIG. 6, it is possible for different wells to be placing different nucleotide sequences 19 on the DNA strand 12.

The synthesizer 32 of FIGS. 4 and 5 has been described in connection with a DNA strand 12 that is tethered by its second end 16 and that has a freely-floating first end 14 to which new nucleotides 18 are added. A disadvantage of this is that the location of the signaling group 28 changes as the DNA strand 12 grows ever larger. This imposes an upper practical limit on the number of nucleotides 18 that can be added. After all, at some point, the length of the DNA strand 12 will become an appreciable fraction of the chamber's size. This will tend to undermine collection efficiency.

One way to avoid this difficulty is to instead tether the first end 14 and to use an enzyme 22 that has the ability to catalyze consecutive reactions without actually releasing its substrate. An enzyme 22 that has this property is referred to herein as a "processive enzyme." In the case where a processive enzyme 22 is used to catalyze the addition of nucleotides 18 to a tethered first end 14, the signaling group 28 will always be at the same location, even as the DNA strand 12 becomes quite long.

Figure 7:
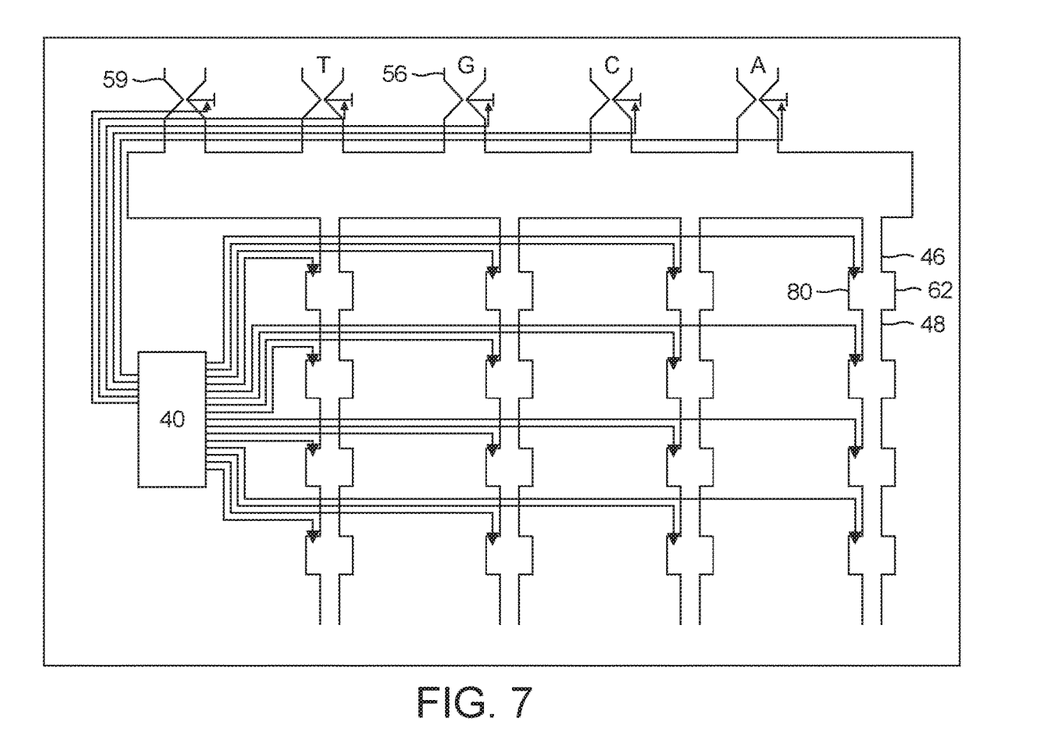
FIG. 7 shows a control system for controlling assembly of nucleotides.

FIG. 7 shows an apparatus for implementing a buffet method for manufacturing different nucleotide sequences 19 in different wells. As was the case in FIG. 6, a substrate has multiple manufacturing units 80. However, instead of each manufacturing unit 80 having its own set of selection valves 50 to control its own sources 54, all the wells 62 share the same sources 54. In this case, the controller 40 instead controls the first and second electrodes 76, 78 at each manufacturing unit 80.

In the buffet method, the controller 40 serves one nucleotide 18 per course. It thus cycles through four courses, one for each nucleotide 20, and then repeats the cycle all over again. If, for a particular manufacturing unit 80, the next nucleotide 20 to be served is not wanted, the controller 40 simply avoids applying a cleaving voltage across the first and second electrodes 76, 80 for that manufacturing unit. In that case, the DNA strand 12 will remain in the state shown in steps (c)-(e) in FIG. 1. As a result, when the loaded carriers 20 carrying that nucleotide 18 is served to that manufacturing unit 80, the blocking group 26 that remains will block any loaded carriers 20 from attaching.

In this method, the controller 40 avoids applying a cleaving voltage until the cleaving time slot just before the next course that brings loaded carriers 20 that have a desired nucleotide 18. Once the controller 40 recognizes that the desired nucleotide 18 will be on its way, it applies a voltage across the first and second electrodes 76, 78 so that the carrier 20 can be removed from the DNA strand 12, thus leaving it exposed and ready to receive a loaded carrier 20 carrying the desired nucleotide 18.

The foregoing implementation is simpler to manufacture. However, there is a loss of throughput since each manufacturing unit 80 may have to wait several courses for its next nucleotide 18 to arrive.

Figure 8:
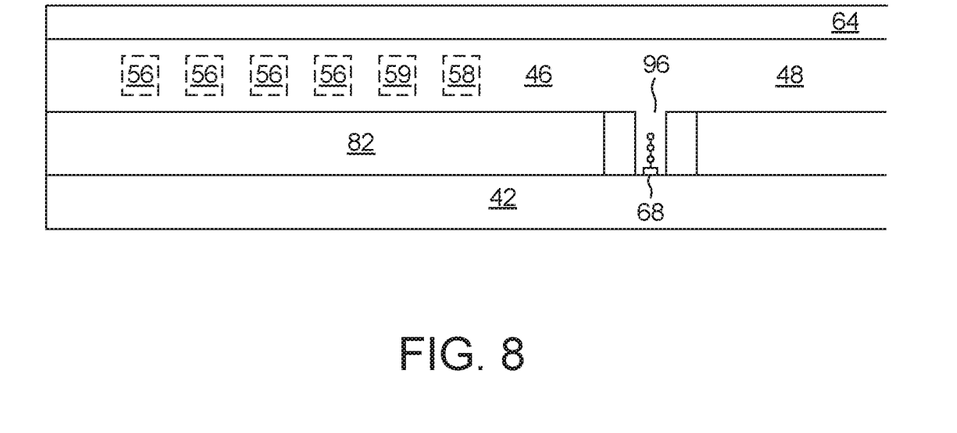
FIGS. 8-10 shows different views of an alternative embodiment of a synthesizer.
Figure 9:
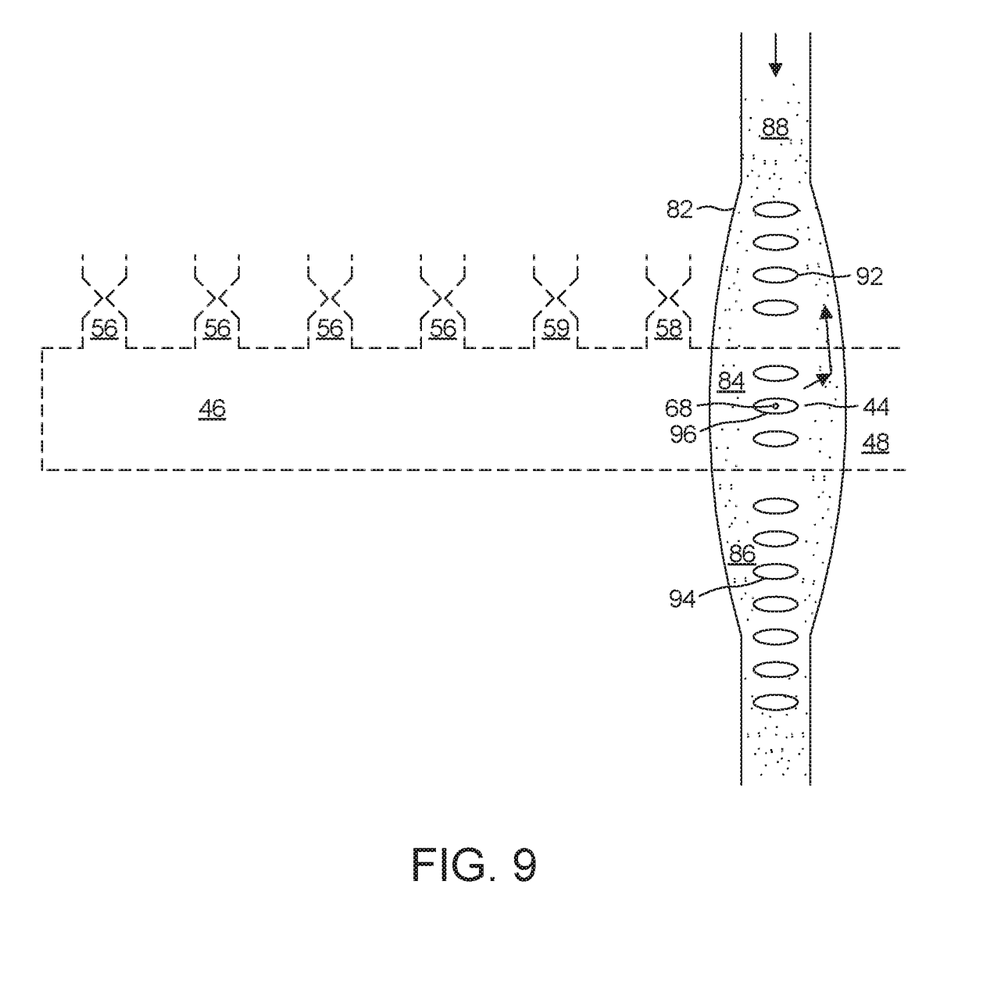
Figure 10:
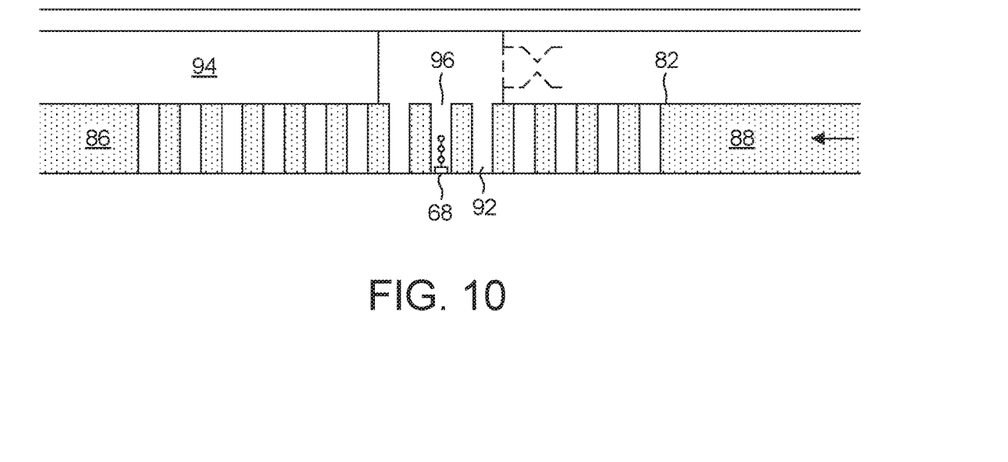

FIG. 8-10 show an embodiment of a synthesizer 32 formed on a substrate 42 having a photonic crystal 82 extending along an axis thereof. In some embodiments, the dielectric used for the photonic crystal 82 is silicon nitride formed in a 200 nm thick layer.

Silicon nitride is a suitable choice in part because of the ease with which one can obtain a high-quality film and because the technology for processing silicon nitride is well-known. Moreover, silicon nitride is relatively easy to functionalize, has a refractive index greater than that of water, and is transparent at the wavelengths of interest. This makes it a good choice for guiding light through a waveguide that contacts an aqueous medium.

On the other hand, silicon nitride's index of refraction, while adequate, is not impressive. Moreover, silicon nitride has a tendency to itself fluoresce. This background fluorescence may interfere somewhat with detection of the signature photon 31.

The illustrated embodiment shows a one-dimensional photonic crystal 82. Such a crystal has high collection efficiency for fluorophores that are oriented perpendicular to the photonic crystal's axis. However, as the fluorophore's axis deviates from this direction, collection efficiency falls off quickly. Thus, when a one-dimensional photonic crystal is used, it is of some importance to control the orientation of the fluorophore.

One way to avoid having to control the orientation of the fluorophore is to use a two-dimensional photonic crystal 82. This is analogous to using a pair of crossed dipoles to ensure capturing a linearly polarized wave with an unknown polarization direction. Such a photonic crystal 82 tends to maintain collection efficiency even when the fluorophore is not exactly normal to the photonic crystal's longitudinal axis.

The use of a two-dimensional photonic crystal 82 imposes constraints on the material. In particular, it becomes preferable that the index of refraction be greater than that required for a one-dimensional photonic crystal 82. Suitable materials for two-dimensional photonic crystals 82 include silicon carbide, diamond, and gallium nitride.

However, it is also possible to chemically control the fluorophore's orientation, thus promoting a good polarization match with even a one-dimensional photonic crystal 82.

One way to exert precise control over the orientation of the fluorophore is to functionalize the substrate using a separate DNA molecule in which the base pairs have been selected to cause it to fold in a particular way. Such a folded DNA molecule, referred to herein as a "DNA origami," could be built using the apparatus and method described in FIGS. 1-4.

The resulting DNA origami attaches to the substrate and forms an attachment point for a processive enzyme 22. The DNA origami has been folded to provide a way to fix the position of the processive enzyme 22. Since the processive enzyme 22 will interact with the nucleotide 18 being attached, and since this nucleotide 18 is attached to a carrier 20 that also has the fluorophore, the DNA origami can also fix the position or orientation of the fluorophore.

Figure 2:
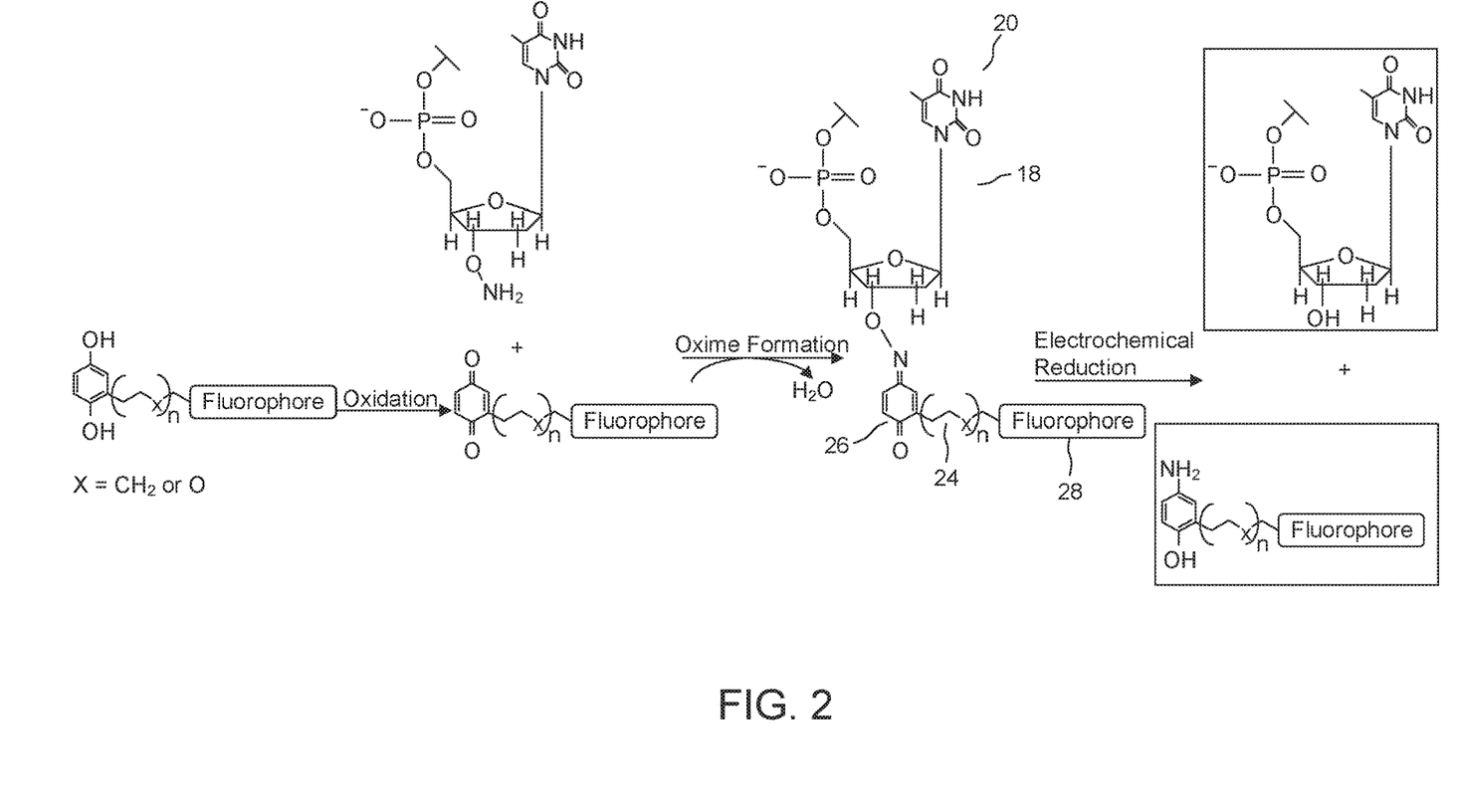
FIGS. 2 and 3 show examples of ways to carry out the cleaving step shown in FIG. 1.

As shown in FIGS. 2 and 3, a linker 24 links the fluorophore to the rest of the loaded carrier 20. The rigidity of this linker 24 provides a basis for controlling the orientation of the signaling group 28, and specifically the fluorophore within that group. By making the linger rigid, it is possible to freeze the fluorophore in a particular desirable confirmation. A more flexible linker 24 permits an external stimulus, such as an electromagnetic field, to influence the fluorophore's orientation.

The photonic crystal 82 includes first and second perforated regions 84, 86 and an imperforated region 88, with the first perforated region 84 being disposed between the second perforated region 86 and the imperforated region 88. The imperforated region 88 and the second perforated region 88 are lengths of dielectric material having a constant width. The first perforated region 84 is a length of dielectric material that is wider at its center and tapers down towards its ends so that it smoothly merges into the imperforated region 88 and the second perforated region. At its center, the first perforated region 84 has a width of about 700 nm. At the edge, it has a width of about 500 nm. The taper follows a parabola having an equation $w=700--x^2$ where x runs from −1 to 1 along the 20-micron length of the imperforated region 88.

A first set of holes 92 arranged in a line perforates the first perforated region 84. The first perforated region 84 is configured to define a cavity that has resonant frequencies overlapping the free-space emission range of the fluorophore. Similarly, a second set of holes 94 perforates the second perforated region 86. The holes 92 are generally elliptical with a major axis extending transverse to the photonic crystal 82 and a minor axis extending along the center of the photonic crystal 82. In a particular embodiment, the centers of the holes 92 are 230 nm apart, and the hole is an elliptical hole having a major axis of 320 nm and a minor axis of 120 nm.

The holes 92 are placed such that a central hole 96 lies at the center of the first perforation region 84. This central hole 96 has a floor 66 with a functionalized spot 68 to which the first end 14 of the DNA strand 12 attaches. In some embodiments, the functionalized spot 68 is a carboxysilane-activated binding spot.

An alternative embodiment, which is equally well-represented by FIGS. 9 and 10, features a first colonnade 84 having a first row of columns 92 arranged in a line perforates the first perforated region 84. The first colonnade 84 is configured to define a cavity that has resonant frequencies overlapping the free-space emission range of the fluorophore. Similarly, a second colonnade 94 features a second row of columns 94. The columns 92 have a generally elliptical cross-section with a major axis extending transverse to the photonic crystal 82 and a minor axis extending along the center of the photonic crystal 82. In a particular embodiment, the centers of the columns 92 are 230 nm apart, and each column's cross-section has a major axis of 320 nm and a minor axis of 120 nm.

The columns 92 are placed such that a pair of adjoining columns 96 defines a floor area 66 at the center of the first colonnade 84. This floor area 66 has a functionalized spot 68 to which the first end 14 of the DNA strand 12 attaches. In some embodiments, the functionalized spot 68 is a carboxysilane-activated binding spot.

Because of the relative ease with which fluid flows around columns, the alternative embodiment with its colonnades offers the advantage of promoting fluid flow to and from the floor area 66 around the functionalized spot 68.

In the first embodiment, it was the second end 16 that attached to the functionalized spot 68. As a result, the nucleotides 18 were being added at a free end (i.e. the first end 14) opposite the tethered end (i.e., the second end 16). The lengthening DNA chain 12 results in the signature photon 31 emerging from a point that grows progressively further from the functionalized spot 68.

The ever-growing distance between the second end 16 and the functionalized spot 68 was not a significant problem in the first embodiment because the chamber 44 was large enough to accommodate very large DNA strands 12.

However, in the second embodiment, the chamber 44 is small enough for this to become a problem. In this second embodiment, as the DNA strand 12 grows past about 500 nanometers, it becomes an appreciable fraction of the chamber's size. This leads to a noticeable drop in collection efficiency. As a result, the DNA strand 12 cannot be made very long. For example, a DNA strand 12 having more than one thousand nucleotides 18 may become impractical to build.

Therefore, in this second embodiment, it is preferable to have the first end 14 be bound to the functionalized spot 68. As a result, the position from which the signature photon 31 begins its journey to the detector 74 stays roughly the same. Also as a result of this difference, the second embodiment requires the use of a processive enzyme 22, such as a processive version of TdT, to attach nucleotides 18 to the DNA strand 12. In some embodiments, such an enzyme 22 is tethered to the functionalized spot 68.

The second embodiment includes a microfluidic system 34 similar to that described in the first embodiment. The excitation system 36 in the second embodiment includes a light source 60 coupled to the photonic crystal 82. The detection system 38 includes a detector 74 coupled to the imperforated region 88. These are similar to those in the first embodiment and are therefore not shown.

Operation proceeds in a manner similar to that described in the first embodiment, and thus need not be described in detail. The difference begins when the light source 60 transmits a pulse of light through the photonic crystal 82. At this point, the fluorophore has an electron that has been promoted to a higher energy level. The detector 74 is thus waiting for this electron to fall to ground state so that it can detect the signature photon 31.

The fluorophore emits the signature photon 31 in response to spontaneous emission of a triggering photon from the vacuum. The photonic crystal 82 is configured to promote such spontaneous emission by providing an optical resonant cavity having a resonance that overlaps with the free-space emission spectra. The fluorophore is then placed into this cavity.

In the second embodiment, an attempt is made to enhance the spontaneous emission rate of the signature photon 31 and to inhibit bleaching of the fluorophore. This is carried out by choosing the geometry of the first set of holes 92 such that a photon having the triggering wavelength is more likely to manifest itself in the synthesizing chamber 44. In particular, the hole geometry and taper within the first perforated region 84 are chosen such that the first perforated region 84 acts as a resonant cavity that promotes spontaneous emission.

The second embodiment thus extends the lifetime, not the fluorescent lifetime but the time until it bleaches, of the fluorophore by encouraging spontaneous emission. This makes it more probable that the fluorophore's excited energy state will decay in a way that results in a signature photon 31, and not a non-radiative pathway such as bleaching.

However, once the fluorophore emits its signature photon 31, there is still the matter of directing it to the detector. After all, upon being emitted, the signature photon 31 has 4π steradians worth of directions to travel in, only some of which will lead to the detector 74.

In the first embodiment, the sidewalls were shaped to approximate a paraboloid. They were therefore able to reflect the signature photon 31 in an appropriate direction.

To carry out an analogous function, the second embodiment relies on its second perforation region 86 and on the geometry of the photonic crystal 82.

Upon being emitted, the signature photon 31 enters the photonic crystal 82. The photonic crystal 82 thus traps it so that it cannot travel in any direction that is transverse to the axis of the photonic crystal 82. However, it can still travel freely along the axis of the photonic crystal 82. Since the detector 74 is at the end of the imperforated region 88, there is a 50% probability that the signature photon 31 will travel in the wrong direction.

The solution adopted in the second embodiment is to cause the second perforation region 86 to function as a reflector. This is achieved by providing a second perforation region 86 that matches the width of the first perforation region 84 and that has a second set of uniformly-sized holes 92, each of which matches the size and shape of that hole in the first perforation region 84 that is closest to the beginning of the second perforation region 86. A photon that begins to propagate in this second perforated region 86 will thus be motivated to turn around and go the other way, namely towards the imperforated region 88 that ultimately leads to the detector 74. This arrangement thus promotes collection efficiency.

Figure 11:
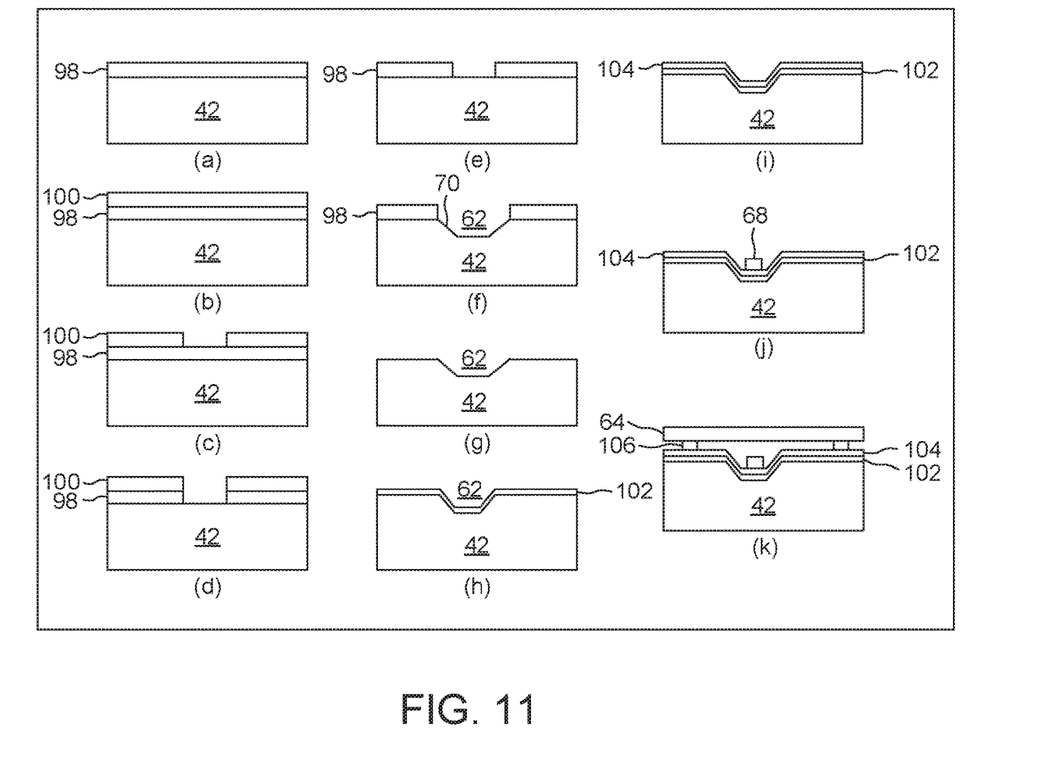
FIG. 11 illustrates steps used in connection with the manufacture of the embodiment shown in FIGS. 4 and 5.

Referring now to FIG. 11, a process for manufacturing the synthesizer 32 shown in FIGS. 4 and 5 begins by growing a silicon dioxide layer 98 on a silicon substrate 42 (step (a)) and then spin-coating a layer of photoresist 100 on the silicon dioxide layer 98 (step (b)). A suitable mask is then made for marking the future positions of the channels 46, 48 and the well 62 (step (c)). The photoresist 100 is then exposed and developed. This is followed by a wet etching step using a buffered oxide etch (fluoride ion etch) (step (d)). The photoresist 100 is then stripped off, leaving behind silicon dioxide layer 98, which has been selectively etched to expose the underlying silicon substrate 42 (step (e)).

The next step is to actually form the liquid-containing features, such as channels 46, 48 and the well 62. This involves a deeper anisotropic etch, typically a wet etching process that relies on exposure to a solution that has a hydroxide anion and either a tetramethylammonium cation or a potassium cation. To reduce undercutting, it is useful to lower the surface tension of the solution. One way to do this is to add a surfactant. A suitable surfactant is non-ionic surfactant such as octylphenol ethoxylate. The resulting channels 46, 48 and well 62 will have sidewalls 70 at an angle dictated by the 111, 110, and 100 planes of the substrate 42 (step (f)). For those embodiments in which the substrate 42 is silicon, this process results in 54.7 degree sidewalls 70 for the exposed <111> planes and 45 degree sidewalls 70 for the exposed <110> planes.

Following this etch, the silicon dioxide layer 98 is stripped off completely. Doing so leaves behind the bare substrate 42, which has now been etched with the channels 46, 48 and the well 62 (step (g)).

Ultimately, the well 62 is expected to reflect signature photons 31 to a detector. Since a bare silicon substrate 42 is not particularly reflective, it is useful at this point to deposit a reflective metal layer 102 within the well 62 (step (h)). Suitable reflective metal layers 102 include those made of copper and those made of aluminum. Next, a dielectric spacer is placed over the reflective metal layer 102 (step (i)). This dielectric spacer is useful to avoid quenching the fluorophore in the event that the fluorophore comes into contact with the metal surface. A suitable dielectric spacer is $Al_2O_3$. The function of the dielectric spacer is to inhibit fluorescence quenching of the fluorophore by the reflective metal layer 102 and to inhibit corrosion of the reflective metal layer 102 by reactant and rinse solutions.

An electron beam or ion beam is then used to place the functionalized spot 68 at the well's floor 66 (step (j)). Although carbon is a suitable material for the functionalized spot 68, it is also possible to use another material, such as silicon dioxide. The functionalized spot 68 could also be created using e-beam lithography, either by directly patterning a negative tone material such as hydrogen silsesquioxane and functionalizing that, or depositing a positive tone resist and defining the functionalization using deposition or gaseous functionalization.

The next step, once the liquid-containing features are ready, is to cover the microfluidic system 34 both to prevent fluid from escaping and to prevent contaminants from entering. This is carried out by placing a pattern of adhesive spots 106 on the dielectric spacer and placing a cover glass 64 on the adhesive spots 106 (step (k)). This process can be carried out using microcontact lithography or aerosol jet printing. Alternatively, a process such as anodic bonding can be used to seal the devices.

The invention claimed is:

1. A nucleotide complex comprising a nucleotide and an electrochemically cleavable blocking group, wherein the electrochemically cleavable blocking group is located on the 3' hydroxyl group of the nucleotide.

2. The nucleotide complex of claim 1, wherein the cleavable blocking group comprises a quinone oxime ether moiety.

3. The nucleotide complex of claim 2, wherein the quinone oxime ether moiety comprises one, or more detectable substituents.

4. The nucleotide complex of claim 3, wherein the detectable substituent comprises a fluorophore.

5. The nucleotide complex of claim 3, wherein the detectable substituent comprises a reactive functional group.

6. The nucleotide complex of claim 5, wherein the reactive functional group comprises a reactive amine with a detectable signal.

7. The nucleotide complex of claim 6, wherein the detectable signal is a fluorescent signal.

8. The nucleotide complex of claim 1, wherein the electrochemically cleavable blocking group comprises a labile functional group comprising an ester, wherein the ester is substituted with a quinone capable of lactonization upon reduction.

9. The nucleotide complex of claim 8, wherein the quinone comprises one, or more, detectable substituents.

10. The nucleotide complex of claim 9, wherein the detectable substituent is a fluorophore.

11. The nucleotide complex of claim 2, wherein the nucleotide of the nucleotide complex has an aminooxy substitution at the 3' position.

12. The nucleotide complex of claim 8, wherein quinone is modified with a functional group selected to form a 6-membered ring upon reduction.

13. The nucleotide complex of claim 12, wherein the functional group is 3-(2,5-dimethyl-3,6-dioxycyclohexa-1,4-dien-1-yl)-methylbutanoic ester.

14. A method for extending a single-stranded DNA chain with one, or more, nucleotides, comprising the steps of:
 a.) contacting a tethered single-stranded DNA chain with the nucleotide complex of claim 3 under conditions suitable for the attachment of the nucleotide complex to the DNA chain;
 b.) confirming attachment of the nucleotide complex to the DNA chain by detecting the detectable substituent on the blocking group of the nucleotide complex; and
 c.) detaching the blocking group of the nucleotide complex from the DNA chain under conditions suitable for electrochemical cleavage of the blocking group from the attached nucleotide;
wherein the nucleotide remains attached to the tethered DNA chain, thereby extending the DNA chain.

15. The method of claim 14, wherein in step c.) the blocking group is cleaved by exposure to an electrical potential difference in a buffered solution.

16. The method of claim 14, wherein in step c.) the blocking group is cleaved by exposure to a suitable reducing agent.

17. A method for extending a single-stranded DNA chain with one, or more, nucleotides, comprising the steps of:
 a.) contacting a tethered single-stranded DNA chain with the nucleotide complex of claim 9 under conditions suitable for the attachment of the nucleotide complex to the DNA chain;
 b.) confirming attachment of the nucleotide complex to the DNA chain by detecting the detectable substituent on the blocking group of the nucleotide complex; and
 c.) detaching the blocking group of the nucleotide complex from the DNA chain under conditions suitable for electrochemical cleavage of the blocking group from the nucleotide;
wherein the nucleotide remains attached to the tethered DNA chain, thereby extending the DNA chain.

* * * * *